United States Patent
Swoyer et al.

(10) Patent No.: US 7,065,412 B2
(45) Date of Patent: Jun. 20, 2006

(54) IMPLANTABLE TRIAL NEUROSTIMULATION DEVICE

(75) Inventors: John M. Swoyer, Andover, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 225 days.

(21) Appl. No.: 10/424,032

(22) Filed: Apr. 25, 2003

(65) Prior Publication Data

US 2004/0215287 A1    Oct. 28, 2004

(51) Int. Cl.
*A61N 1/18* (2006.01)
(52) U.S. Cl. ............... 607/117; 607/48; 607/116
(58) Field of Classification Search .......... 607/40, 607/41, 46, 48, 34, 117, 116
See application file for complete search history.

(56) References Cited

U.S. PATENT DOCUMENTS

| | | | |
|---|---|---|---|
| 6,301,502 B1 * | 10/2001 | Owen et al. | 607/5 |
| 6,360,750 B1 | 3/2002 | Gerber et al. | |
| 6,453,198 B1 * | 9/2002 | Torgerson et al. | 607/29 |
| 6,553,263 B1 * | 4/2003 | Meadows et al. | 607/61 |
| 6,687,538 B1 * | 2/2004 | Hrdlicka et al. | 607/2 |
| 6,847,849 B1 | 1/2005 | Mamo et al. | |
| 6,941,171 B1 | 9/2005 | Mann et al. | |

* cited by examiner

*Primary Examiner*—Jeffrey R. Jastrzab
*Assistant Examiner*—Alyssa M. Alter
(74) *Attorney, Agent, or Firm*—Anna M. Nelson; Thomas F. Woods

(57) ABSTRACT

The invention provides an implantable trial neurostimulator. The implantable trial neurostimulator may be equipped with limited, short-term battery resources. The limited battery resources are designed to last for a finite period of time, thereby preventing a patient or physician from prolonging the trial neurostimulation period. For example, the implantable trial neurostimulator may be designed to stop functioning after a number of days or weeks, upon exhaustion of the battery resources. Alternatively, the implantable trial neurostimulator may be disabled upon expiration of a timer. The trial neurostimulator may be temporarily implanted in a subdural pocket in which the chronic stimulator is ultimately implanted. In this manner, the trial neurostimulator can be coupled to a chronic lead and avoid any percutaneous connections, reducing the risk of infection and affording greater convenience and comfort to patients.

12 Claims, 8 Drawing Sheets

IMPLANTABLE TRIAL NEUROSTIMULATION DEVICE

FIELD OF THE INVENTION

The invention relates generally to neurostimulation and, more particularly, to trial neurostimulation to evaluate efficacy and patient acceptance of neurostimulation.

BACKGROUND

A variety of pelvic floor disorders such as urinary control disorders, fecal control disorders, interstitial cystitis, sexual dysfunction, and pelvic pain are influenced by the sacral nerves. In particular, the organs involved in various bodily functions receive much of their control via the second, third, and fourth sacral nerves, commonly referred to as S2, S3, and S4, respectively. The sacrum, in general, is a large, triangular bone situated at the lower part of the vertebral column, and at the upper and back part of the pelvic cavity. The spinal canal runs throughout the sacrum. The sacral nerves pass through the sacrum via the anterior and posterior sacral foramina. These organs are also innervated via other nerves, such as the pudendal nerve.

Electrical stimulation of the sacral nerves, pudendal nerves, and other nerves of the pelvic floor has been found to offer relief for many pelvic floor disorders. For example, medical leads having discrete electrodes are implanted on and near the sacral nerves. An implantable pulse generator drives the electrodes with an electrical signal to stimulate the sacral nerves, and thereby restore or control bodily functions affected by pelvic floor disorders. Several techniques of electrical stimulation may be used, including stimulation of nerve bundles within the sacrum.

Chronic implantation of a pulse generator and lead for sacral nerve stimulation is typically preceded by a trial period. The trial period ordinarily has a prescribed maximum duration, but sometimes is exceeded by the patient or the physician. During the trial period, a clinician evaluates the efficacy of sacral nerve stimulation in alleviating the patient's disorder to determine whether the patient is a good candidate for chronic implantation.

The trial period ordinarily involves implantation of a temporary or chronic lead, and percutaneous connection of the lead to an external trial stimulator. Often, connection of the lead to the trial stimulator involves extensive subcutaneous tunneling of the lead to a percutaneous exit site. In addition, the percutaneous connection presents a significant risk of infection. Indeed, to reduce infection risk, the lead is ordinarily tunneled away from the site selected for chronic implant, requiring added time and effort by the surgeon.

U.S. Published Patent Application No. 20020147485 to Mamo et al. describes minimally invasive implantation of a sacral stimulation lead for percutaneous connection to a trial stimulator or subcutaneous connection to a chronic implantable stimulator. U.S. Published Patent Application No. 20020055761 to Mann et al. describes subcutaneous tunneling of a lead to a percutaneous exit site for connection to a trial stimulator. U.S. Pat. No. 6,360,750 to Gerber et al. describes the connection of an implanted sacral nerve lead to a test stimulator for use in screening a patient for implantation of a chronic stimulator. Table 1 below lists documents that disclose trial neurostimulation systems.

TABLE 1

| Patent Number | Inventors | Title |
|---|---|---|
| 20020147485 | Mamo et al. | Minimally invasive apparatus for implanting a sacral stimulation lead |
| 20020055761 | Mann et al. | Implantable stimulator systems and methods for treatment of incontinence and pain |
| 6,360,750 | Gerber et al. | Minimally invasive surgical techniques for implanting devices that deliver stimulant to the nervous system |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY

The present invention is directed to an implantable trial neurostimulation device. The invention has certain objects. That is, various embodiments of the present invention provide solutions to one or more problems existing in the prior art with respect to the trial neurostimulation for evaluation of efficacy and patient acceptance of neurostimulation.

Such problems include, for example, the time and effort involved in implantation, tunneling and percutaneous connection of nerve leads to external trial stimulators. In addition, the problems include the risk of infection posed by the percutaneous interconnection. Another problem concerns the inconvenience and discomfort presented by a percutaneous connection, and the need to carry an external trial stimulator during the course of the patient's daily routine during a trial neurostimulation period. A further problem pertains to the ability of the patient or physician to prolong the trial neurostimulation period for an extended period of time.

Various embodiments of the present invention have the object of solving at least one of the foregoing problems. For example, it is an object of the present invention to reduce the amount of time and effort required for connection of a nerve lead and a trial stimulator. It is a further object of the invention to reduce infection risks during the trial neurostimulation period. Another object is to eliminate the need for the patient to carry an external trial stimulator during the trial neurostimulation period. An additional object is to more effectively control the maximum duration of the trial neurostimulation period.

Various embodiments of the invention may possess one or more features capable of fulfilling the above objects. In general, the invention provides an implantable trial neurostimulator. The neurostimulator may include one or more leads positioned to stimulate sacral nerves, pudendal nerves, perineal nerves, or other areas of the nervous system. In accordance with the invention, the implantable trial neurostimulator is equipped with limited battery resources. The limited battery resources are designed to last for a finite period of time, thereby preventing a patient or physician from prolonging the trial neurostimulation period. For example, the implantable trial neurostimulator may be designed to stop functioning after a number of days, weeks, or months, either upon exhaustion of the battery resources or expiration of a timer. The limited battery resources may be realized by a small, commercially available battery that affords opportunities for reduction in the size of the implantable trial neurostimulator relative to the size of an implantable chronic neurostimulator. The trial neurostimulator may be temporarily implanted in a subdural pocket in which the chronic stimulator is ultimately implanted.

In comparison to known implementations of trial neurostimulators, various embodiments of the present invention may provide one or more of advantages. For example, the trial neurostimulator is implanted and need not be carried by the patient, offering convenience and comfort. As a further advantage, implantation of the trial neurostimulator in the chronic implant site reduces the amount of lead tunneling that must be performed by the surgeon, as the chronic implant site typically will be disposed relatively close to the nerve stimulation site. Also, the implantable trial neurostimulator eliminates the need for a percutaneous connection, and thereby reduces the risk of infection to the patient during the trial period. As another advantage, the limited battery resources provided in the implantable trial neurostimulator are designed to last for a finite period of time, thereby preventing a patient or physician from prolonging the trial neurostimulation period. Further, the absence of a percutaneous connection makes the trial neurostimulator easier to tolerate, and presents a reduced infection risk, permitting trial periods to run for extended period of times.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
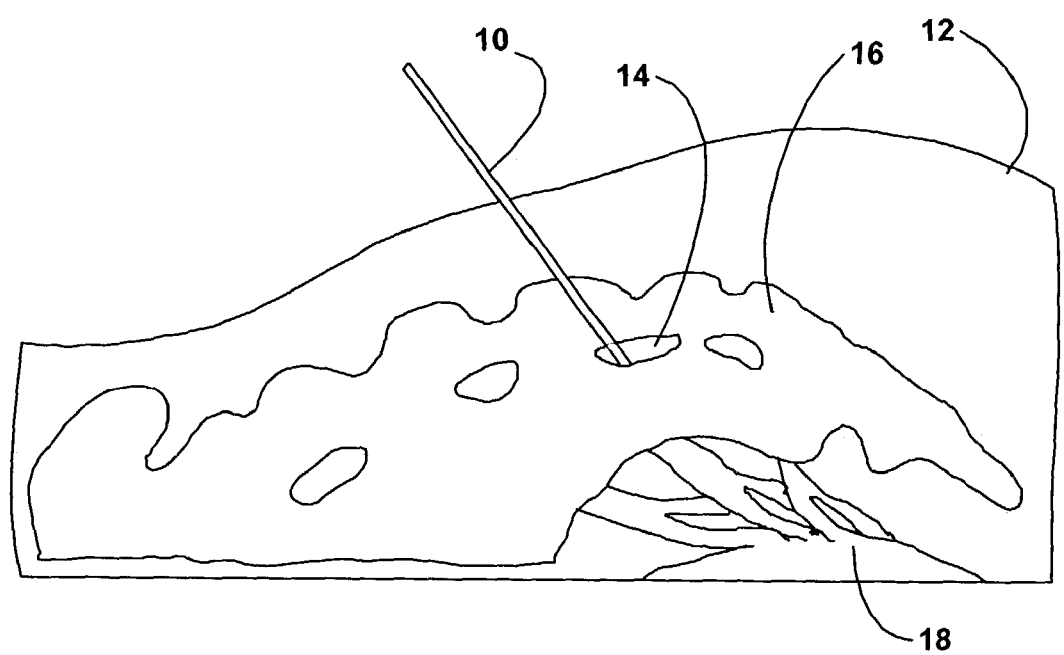
FIG. 1 is a diagram illustrating implantation of a nerve stimulation lead.

FIG. 1 is a diagram illustrating implantation of a nerve stimulation lead 10 for use in a trial neurostimulation period to evaluate efficacy and patient acceptance of sacral nerve stimulation. In the example of FIG. 1, lead 10 is inserted into body 12 of a patient, and implanted into one of dorsal foramen 14 of sacrum 16. However, lead 10 alternatively may be positioned to stimulate pudendal nerves, perineal nerves, or other areas of the nervous system. As further alternatives, lead 10 may be positioned for temporary spinal cord stimulation for the treatment of pain, or for gastric stimulation for the treatment of gastric mobility disorders and obesity. Sacral nerve stimulation will be described herein for purposes of illustration.

Lead 10 may be implanted via a needle stylet for minimal invasiveness. Positioning of lead 10 may be aided by imaging techniques, such as fluoroscopy. The effect of different electrodes carried by lead 10 on sacral nerves 18 may be tested with a test stimulator before selecting a final lead depth. Lead 10 can be implanted for a variety a purposes such as to treat pelvic floor disorders. In some embodiments, a plurality of stimulation leads may be provided. As will be described, lead 10 is coupled to an implantable trial neurostimulator either directly or via a lead extension. In either case, there is no need for a percutaneous connection between lead 10 and the trial neurostimulator.

Figure 2:
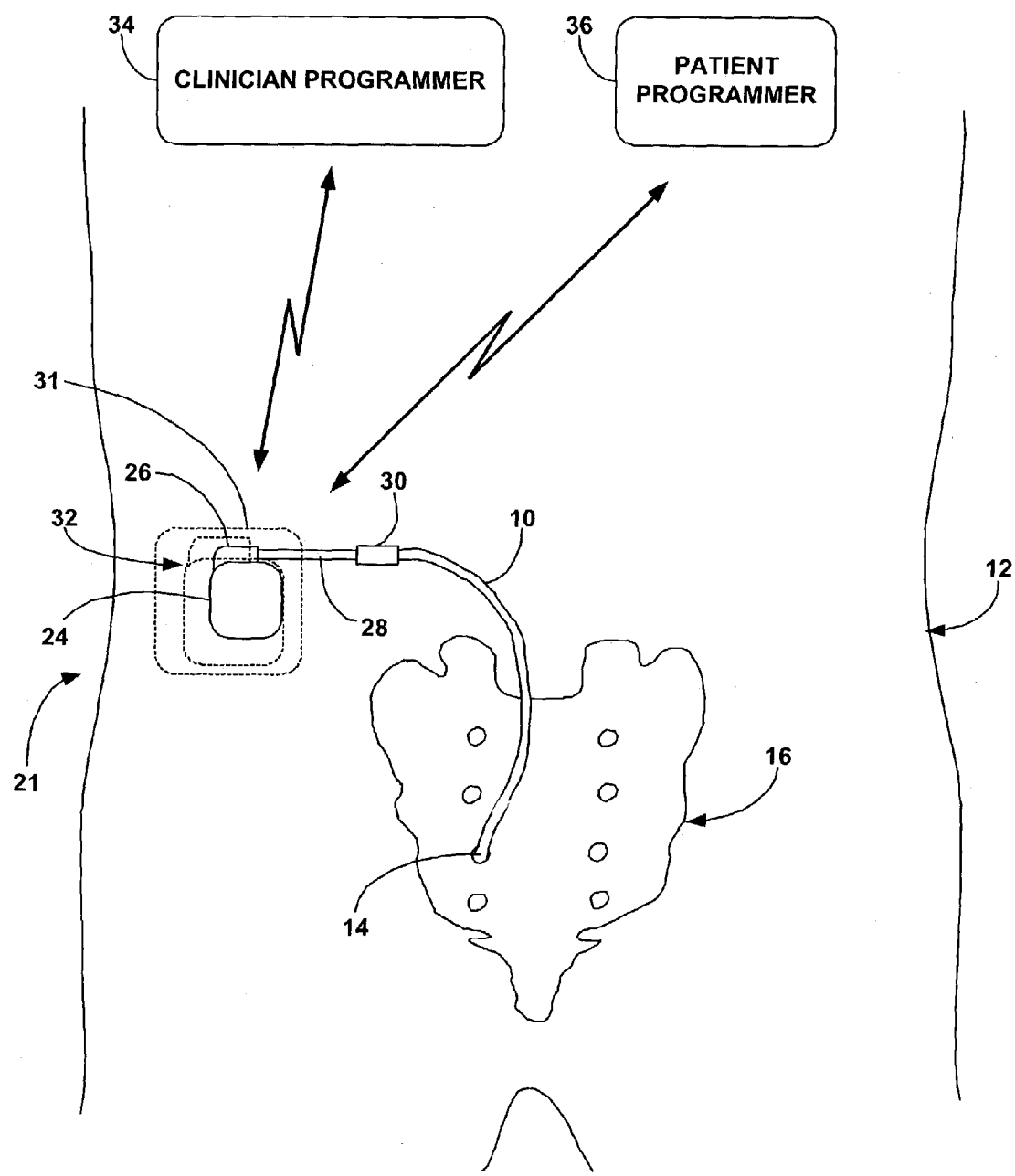
FIG. 2 is a diagram illustrating an implantable trial neurostimulation system for evaluation of nerve stimulation.

FIG. 2 is a diagram illustrating an implantable trial neurostimulation system 21 for evaluation of sacral nerve stimulation via lead 10. Trial neurostimulation system 21 alternatively may be used as a cost-effective means to evaluate neurostimulation for new indications, or indications that require only short term, temporary neurostimulation, e.g., post-operative retention or post-operative pain.

Trial neurostimulation system 21 delivers neurostimulation to the sacral nerves or other regions of the nervous system known to treat pelvic floor disorders urinary control disorders, fecal control disorders, interstitial cystitis, sexual dysfunction, and pelvic pain. As shown in FIG. 2, system 21 includes lead 10 and an implantable trial neurostimulator 24.

Trial neurostimulator 24 includes an implantable pulse generator, and delivers neurostimulation therapy to patient 12 in the form of electrical pulses generated by the implantable pulse generator. In the example of FIG. 2, trial neurostimulator 24 is implanted in the upper left buttock of patient 12, but may be implanted at other locations.

A proximal end of stimulation lead 10 is coupled to a connector block 26 associated with trial neurostimulator 24. In the example of FIG. 2, lead 10 is coupled to connector block 26 via a lead extension 28 and connector 30. Trial neurostimulator 24 can be implanted within the same subdural pocket 31 that serves as the implant site for a chronic neurostimulator following the trial period.

The implant site for trial neurostimulator 24 may serve to avoid the excessive subcutaneous tunneling otherwise required for percutaneous connection to an external trial neurostimulator. In addition, implantable neurostimulator 24 eliminates the need for any percutaneous connection, reducing the risk of infection and affording greater convenience and comfort to the patient. Further, the absence of a percutaneous connection makes the trial neurostimulator easier to tolerate, and presents a reduced infection risk, permitting trial periods to run for extended period of times. Accordingly, the trial period may run for days, weeks or even months, in view of heightened patient tolerance. As examples, the trial period may be less than one month or, in some cases, less than six months.

Notably, as shown in FIG. 2, trial neurostimulator 24 may be significantly smaller than the chronic neurostimulator, indicated by reference numeral 32. In particular, in view of its limited use in the trial period, trial neurostimulator 24 can be equipped with a much smaller and lower capacity battery than chronic neurostimulator 32. In addition, the limited usage of trial neurostimulator 24 may permit the use of less expensive batteries, including commercial available coin cell batteries and the like.

Lead 10 carries one or more stimulation electrodes to permit delivery of electrical stimulation to sacral nerves. For example, implantable trial neurostimulation system 21 may stimulate organs involved in urinary, fecal or sexual function via C-fibers or sacral nerves at the second, third, and fourth sacral nerve positions, commonly referred to as S2, S3, and S4, respectively. Also, in some embodiments, lead 10 may carry one or more sense electrodes to permit trial neurostimulation device 24 to sense electrical signals within sacrum 16.

Accordingly, lead 10 includes an outer lead body that contains one or more conductors to electrically couple the electrodes to terminals within connector block 26. In some embodiments, trial neurostimulator 24 may be coupled to two or more leads deployed at different positions relative to the spinal cord or sacral nerves.

As further shown in FIG. 2, implantable trial neurostimulation system 21 also may include a clinician programmer 34 and a patient programmer 36. Clinician programmer 34 may be a handheld computing device that permits a clinician to program neurostimulation therapy for patient 12, e.g., using input keys and a display. For example, using clinician programmer 34, the clinician may specify neurostimulation parameters for use in delivery of neurostimulation therapy.

Clinician programmer 34 supports radio frequency telemetry with trial neurostimulator 24 to download neurostimulation parameters and, optionally, upload operational or physiological data stored by trial neurostimulator. In this manner, the clinician may periodically interrogate trial neurostimulator 24 to evaluate efficacy and, if necessary, modifies the stimulation parameters.

Like clinician programmer 34, patient programmer 36 may be a handheld computing device. Patient programmer 36 may also include a display and input keys to allow patient 12 to interact with patient programmer 36 and implantable trial neurostimulator 24. In this manner, patient programmer 36 provides patient 12 with an interface for control of neurostimulation therapy by neurostimulator 24.

For example, patient 12 may use patient programmer 36 to start, stop or adjust neurostimulation therapy during the trial period. In particular, patient programmer 36 may permit patient 12 to adjust stimulation parameters such as duration, amplitude, pulse width and pulse rate, within an adjustment range specified by the clinician via clinician programmer 34.

Trial neurostimulator 24, clinician programmer 34 and patient programmer 36 may communicate via wireless communication, as shown in FIG. 1. Clinician programmer 34 and patient programmer 36 may, for example, communicate via wireless communication with trial neurostimulator 12 using RF telemetry techniques known in the art. Clinician programmer 34 and patient programmer 36 also may communicate with each other using any of a variety of local wireless communication techniques, such as RF communication according to the 802.11 or Bluetooth specification sets, or other standard or proprietary telemetry protocols.

Figure 3:
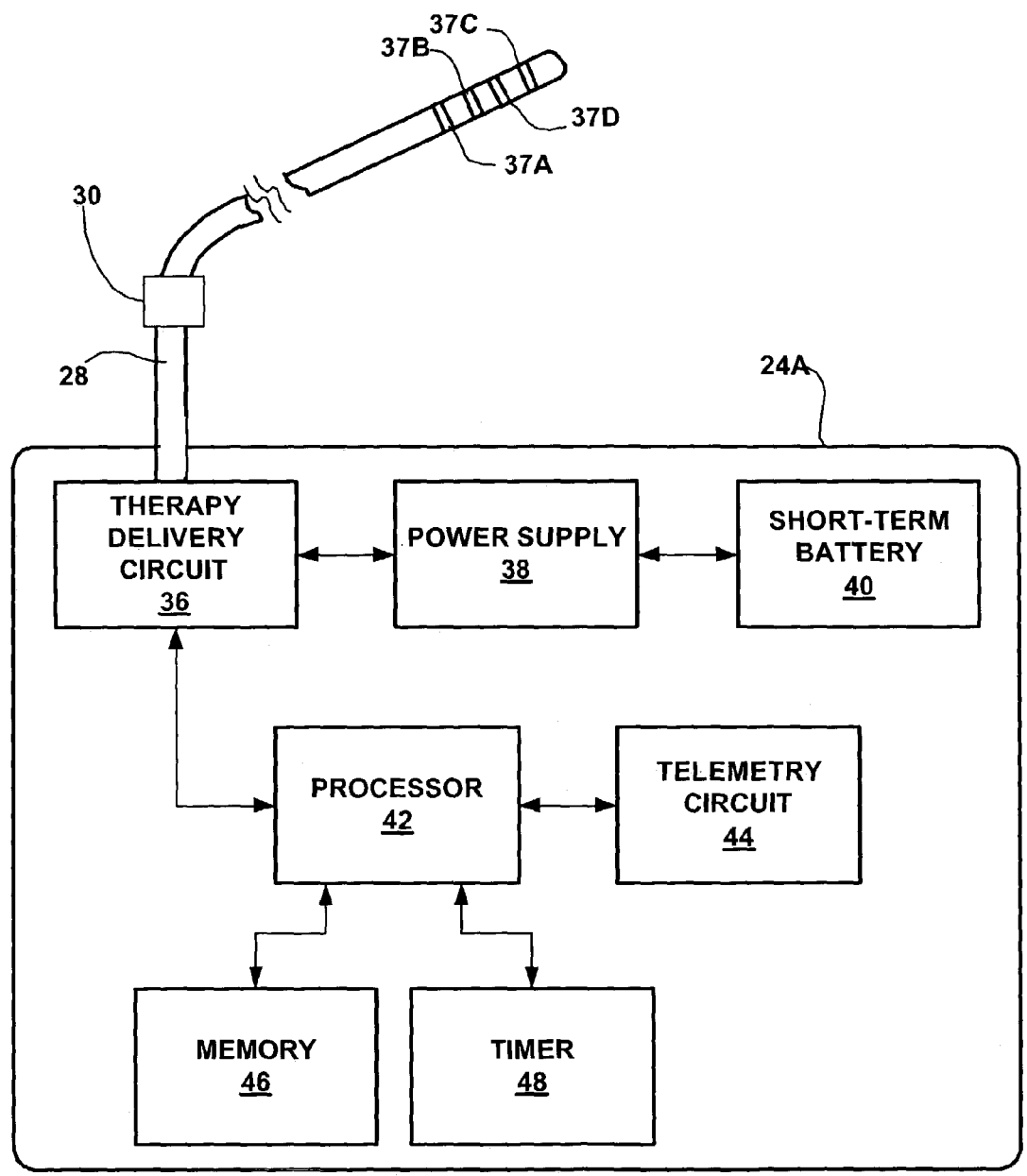
FIG. 3 is a block diagram illustrating various components of an implantable trial neurostimulation device.

FIG. 3 is a block diagram illustrating various components of an implantable trial neurostimulator 24a. As shown in FIG. 2, device 12 delivers neurostimulation therapy via electrodes 37A, 37B, 37C, 37D of lead 10 (collectively "electrodes 37"). Electrodes 37 may be ring electrodes. The configuration, type and number of electrodes 37 illustrated in FIG. 2 are merely exemplary. Electrodes 37 are electrically coupled to a therapy delivery circuit 36 via lead 14.

Therapy delivery circuit 36 may, for example, include an implantable pulse generator coupled to a power supply 38 that generates stimulation energy from power delivered by a short-term battery 40. The implantable pulse generator within therapy delivery circuit 36 delivers electrical pulses to patient 12 via at least some of electrodes 37 under the control of a processor 42. In general, therapy delivery circuit 36 may deliver neurostimulation pulses with an amplitude in the range of approximately 1 to 10 volts, at a frequency in the range of approximately 5 to 150 Hz, for a duration of approximately 1 to 5 minutes, or continuously in some cases.

Processor 42 controls the implantable pulse generator within therapy delivery circuit 36 to deliver neurostimulation therapy according to selected stimulation parameters. Specifically, processor 42 controls therapy delivery circuit 36 to deliver electrical pulses with selected amplitudes, pulse widths, and rates specified by the programs. In addition, processor 42 also controls therapy delivery circuit 36 to deliver the neurostimulation pulses via selected subsets of electrodes 37 with selected polarities.

Processor 42 may control therapy delivery circuit 36 to deliver each pulse according to a different program, thereby interleaving programs to simultaneously treat different symptoms or provide a combined therapeutic effect. For example, in addition to treatment of urinary incontinence, trial neurostimulator 24A may be configured to deliver neurostimulation therapy to treat pain. Processor 42 may include a microprocessor, a controller, a DSP, an ASIC, an FPGA, discrete logic circuitry, or the like.

Trial neurostimulator 24A also includes a memory 30. In some embodiments, memory 46 stores multiple sets of stimulation parameters that are available to be selected by patient 12 for delivery of neurostimulation therapy. For example, memory 30 may store stimulation parameters transmitted by clinician programmer 21. Memory 30 also stores program instructions that, when executed by processor 28, cause device 12 to deliver neurostimulation therapy.

Memory 30 may include any volatile, non-volatile, magnetic, optical, or electrical media, such as a RAM, ROM, CD-ROM, hard disk, removable magnetic disk, memory cards or sticks, NVRAM, EEPROM, flash memory, and the like. Accordingly, the invention also contemplates computer-readable media storing instructions to cause processor 42 to provide the functionality described herein.

A telemetry circuit 44 supports wireless communication between device 12, clinician programmer 34, and patient programmer 36. In addition, in some embodiments, trial neurostimulator 24A may optionally include a timer 48. Timer 48 may serve to time the duration of the trial period. For example, upon initiation of the trial period, timer 48 starts running to track the elapsed time in the trial period relative to a maximum trial period time. In some embodiments, when timer 48 expires, processor 42 responds by disabling therapy delivery circuit 36. In other words, processor 42 stops the trial period by stopping delivery of neurostimulation therapy to patient 12 by trial neurostimulator 24A.

In this manner, implantable trial neurostimulator 24A can be configured to prevent patient 12 or a physician from prolonging the trial period beyond a prescribed period of time. Rather, implantable trial neurostimulator 24A has a finite period of operation, determined by a maximum trial period that may be specified at the factory or in a programmable manner by a physician. Timer 48 may be implemented in hardware using a real-time clock, in software by processor 42, or a combination thereof. Accordingly, timer 48 is illustrated as a separate component in FIG. 3 merely for exemplary purposes.

As an alternative to the use of timer 48, short-term battery 40 of implantable trial neurostimulator 24A may be selected based on the amount of battery resources available from the battery relative to the desired length of the trial period. In other words, short-term battery 40 may be selected with the explicit intention that it will only last for a short period of time commensurate with the trial period.

Short-term battery 40 is selected such that the battery is exhausted below a usable level within a predetermined trial period of time. If the desired trial period in one week, for example, short-term battery 40 is selected to last only approximately one week before power is exhausted, given a known range of rate of power consumption by implantable trial neurostimulator 24A.

When short-term battery 40 is exhausted, trial neurostimulator 24 stops functioning, and the trial period is therefore over. Accordingly, differently sized batteries can be selected for different desired trial periods. The use of a short-term battery 40 serves an objective that is essentially the opposite of batteries ordinarily used in implantable neurostimulators, i.e., the short-term battery ensures short life span for trial neurostimulator 24A rather than neurostimulator longevity.

As examples of short-term batteries, trial neurostimulator 24A may incorporate a variety of commercially available batteries such as lithium, NiCad, Nickel-metal-hydride or other batteries ordinarily used in watches, cameras and the like. In some embodiments, short-term battery 40 may take the form of a coin cell battery that reduces the size and profile of trial neurostimulator 24A relative to typical chronic neurostimulators. Short-term battery 40 may be selected to deliver power in the range of approximately 30 to 200 milliamp-hours (mAh). Again, the precise power range will depend on the desired length of the trial period in view of known power consumption requirements of trial neurostimulator 24A.

Figure 4:
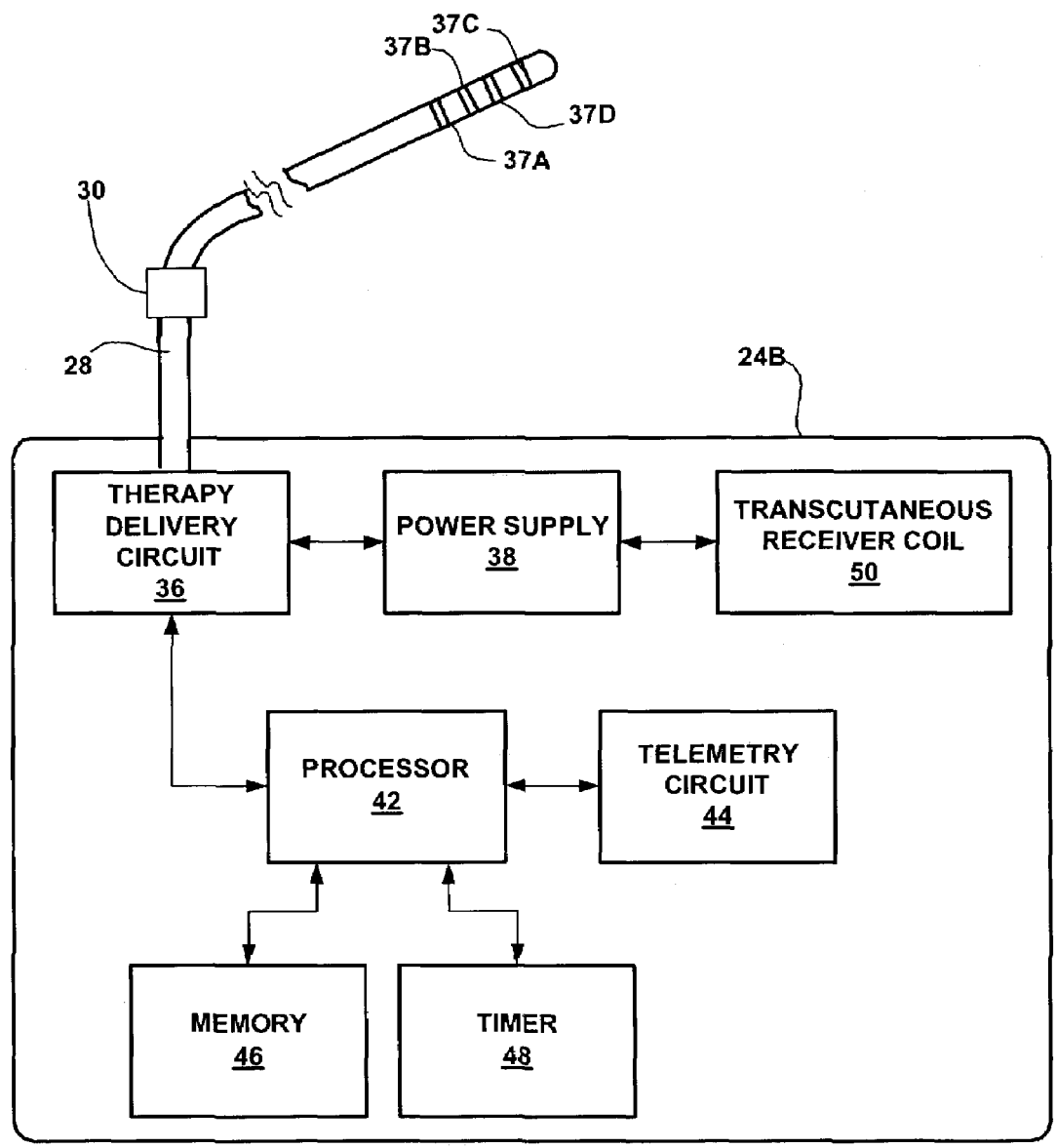
FIG. 4 is a block diagram illustrating various components of another implantable trial neurostimulation device.

FIG. 4 is a block diagram illustrating various components of another implantable trial neurostimuiator 24B. Trial neurostimulator 24B conforms substantially to trial neurostimulator 24A, but incorporates a transcutaneous receiver coil 50 instead of a battery 40. Transcutaneous receiver coil 50 is implanted with trial neurostimulator 24B and transduces electromagnetic energy receive from an external coil into power for power supply 38. In this embodiment, trial neurostimulator 24B does not rely on limited battery resources to control the duration of the trial period. Instead, trial neurostimulator 24B receives power via transcutaneous receiver coil 50 and controls the duration of the trial period in response to timer 48.

Figure 5:
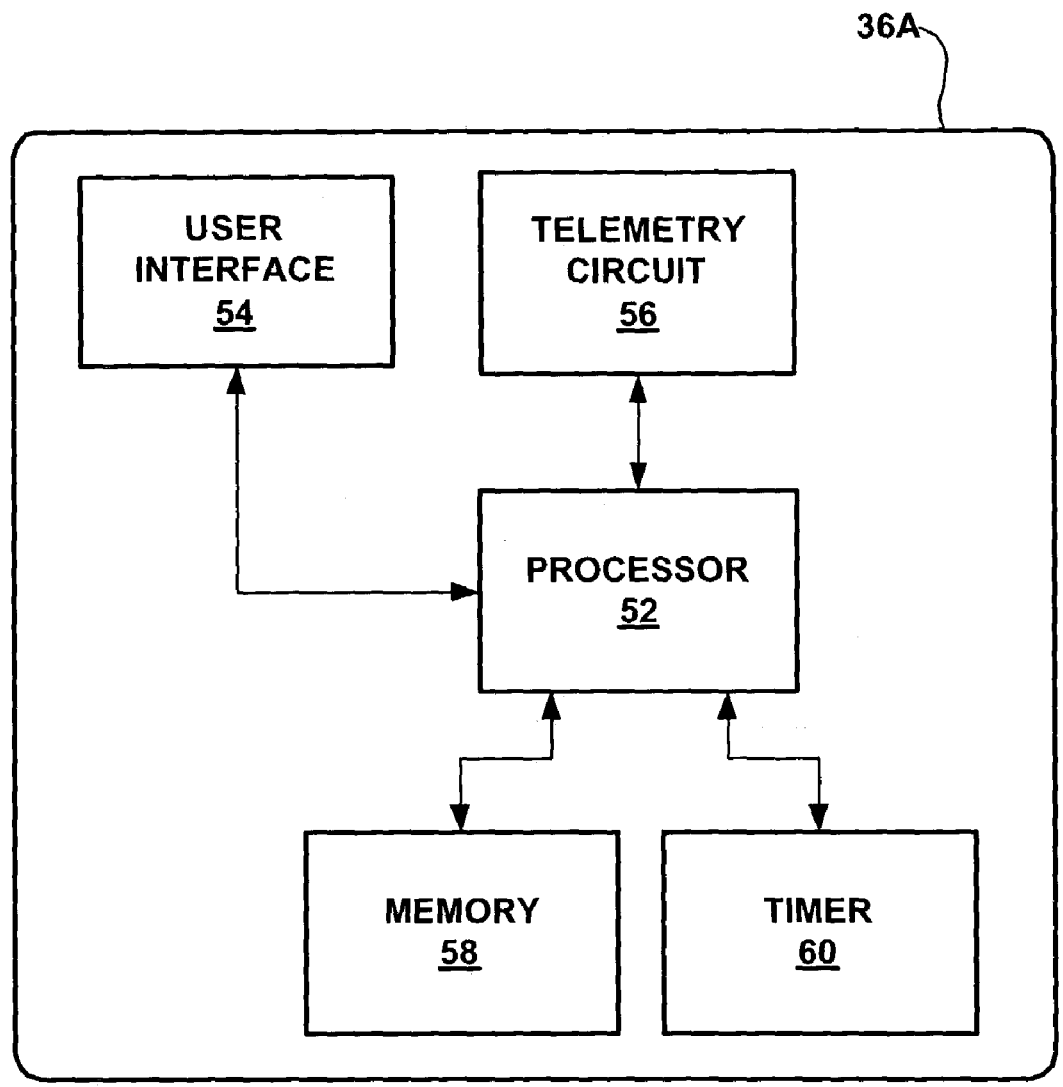
FIG. 5 is a block diagram illustrating various components of a patient programmer for use with the implantable trial neurostimulation system of FIG. 2.

FIG. 5 is a block diagram illustrating various components of a patient programmer 36A for use with the implantable trial neurostimulation system 21 of FIG. 2. As shown in FIG. 5, patient programmer 36A includes a processor 52, a user interface 54, and a telemetry circuit 56 for communication with telemetry circuit 44 of either of trial neurostimulators 24A, 24B. Patient programmer 36A also includes memory 58 to store parameters, settings and instructions, and optionally a timer 60. Timer 60 may be implemented in hardware or software, and may operate as a programmable feature of processor 52.

Patient programmer 36A responds to user input entered via user interface 54 to adjust stimulation parameters, settings, and the like. In addition, patient programmer 36A may interrogate trial neurostimulator 24 to obtain parameters, settings, and other operational data. For example, patient programmer 36A may be used to initially program trial neurostimulator 24 for the trial period, and to upload parameters, settings, and other operational data from trial neurostimulator 24 upon expiration of the trial period. During the course of the trial period, trial neurostimulator 24 may store a variety of information concerning adjustments made by the user, usage profiles and the like.

Notably, patient programmer 36A is physically decoupled from trial neurostimulator 24 in the sense that the trial neurostimulator is implanted and the patient programmer is external to patient 12. In addition, in some embodiments, patient programmer 36A may be the same patient programmer used with the chronic neurostimulator that is implanted following the trial period. Accordingly, patient programmer 36A may upload applicable parameters, settings, and operational information from trial neurostimulator 24 at the end of the trial period, and then download that information directly to the chronic neurostimulator, providing significant convenience to the physician.

Patient programmer 36A may operate with a rechargeable or replaceable battery (not shown). In the example of FIG. 5, it is assumed that trial neurostimulator 24 includes its own battery. In other embodiments, as described herein, patient programmer 36A may deliver power to trial neurostimulator 24 transcutaneously. In addition, rather than download operational parameters and settings to trial neurostimulator 24 for substantially independent operation by the neurostimulator, patient programmer 36A may dynamically control the operation of the trial neurostimulator by continuous communication with the trial neurostimulator via telemetry circuit 44.

In addition, in some embodiments, patient programmer 36A, rather than trial neurostimulator 24, may control the end of the trial period. For example, processor 52 may be responsive to expiration of a period of time, as indicated by timer 60. In this case, processor 52 transmits a signal to implanted trial neurostimulator 24 instructing the neurostimulator to cease operation. In some embodiments, it may be possible to pay a fee to reactivate trial neurostimulator 24 for a limited period of time. To avoid prolonged use, however, it is generally desirable to disable neurostimulator 24 after a finite period of time.

Alternatively, processor 52 may terminate communication with trial neurostimulator 24, in which case the trial neurostimulator terminates operation. Accordingly, termination of the trial period may be initiated within trial neurostimulator 24 or within patient programmer 36A, and may be accomplished in a variety of ways.

Figure 6:
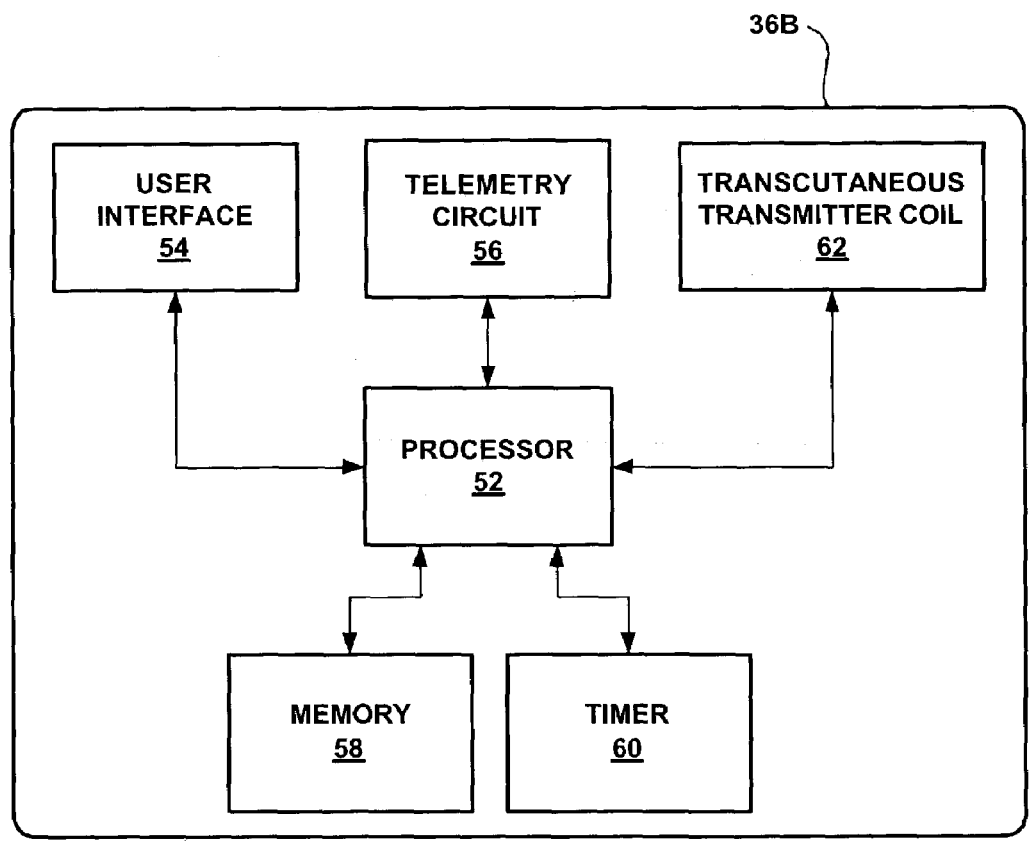
FIG. 6 is a block diagram illustrating various components of another patient programmer for use with the implantable trial neurostimulation system of FIG. 2.

FIG. 6 is a block diagram illustrating various components of another patient programmer 36B for use with the implantable trial neurostimulation system 21 of FIG. 2. Patient programmer 36B conforms substantially to patient programmer 36A of FIG. 5. However, patient programmer 36B further includes a transcutaneous transmitter coil 62 to deliver electromagnetic energy to transcutaneous receiver coil 50 of trial neurostimulator 24B for transformation into operating power.

Accordingly, patient programmer 36B is worn by the patient. Patient programmer 36B, or at least transcutaneous transmitter coil 62, is positioned adjacent trial neurostimulator 24 to provide effective electromagnetic coupling between the transcutaneous transmitter coil and transcutaneous receiver coil 50. In the example of FIG. 6, termination of the trial period can be made by simply terminating the supply of power from transcutaneous transmitter coil 62 and transcutaneous receiver coil 50.

Figure 7:
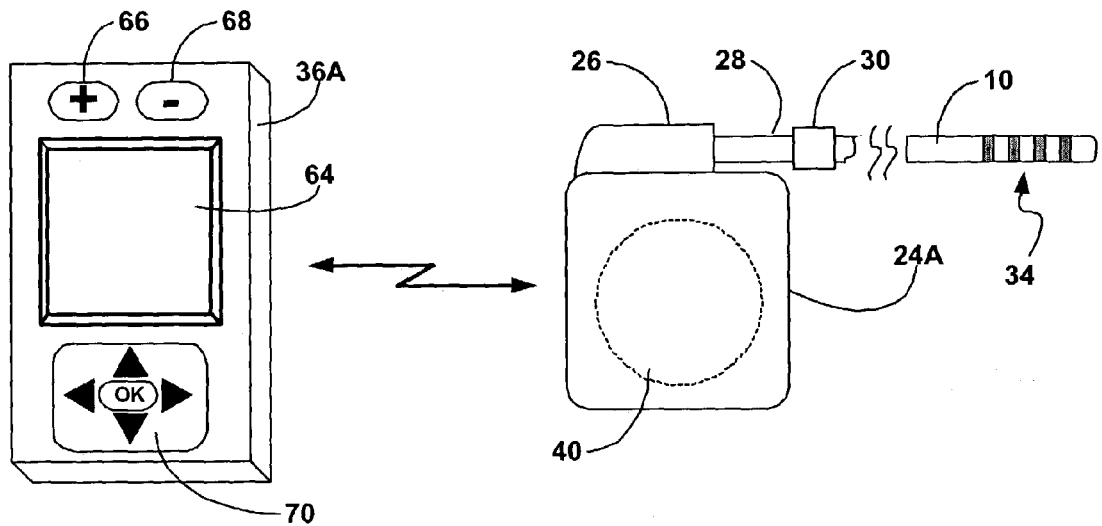
FIG. 7 is a diagram of an implantable trial neurostimulation device with a small battery as a power source.

FIG. 7 is a diagram of an implantable trial neurostimulator 24A with a small, short-term battery 40 as a power source. In the example of FIG. 7, battery 40 is depicted as a coin cell battery, although other battery configurations may be used. In general, battery 40 may be small, inexpensive, and have a substantially reduced power capacity and longevity relative to batteries used in chronic neurostimulators.

FIG. 7 also depicts patient programmer 36A. As shown in FIG. 7, patient programmer 24A may include buttons 66, 68 to increase and decrease stimulation settings, respectively. In addition, patient programmer 36A includes a display 64, and navigational buttons 70 to permit navigation and selection of control options presented via the display. Buttons 66, 68, 70 and display 64 form part of user interface 54. In some case, display 64 may present information advising patient 12 that expiration of the trial period is approaching.

Figure 8:
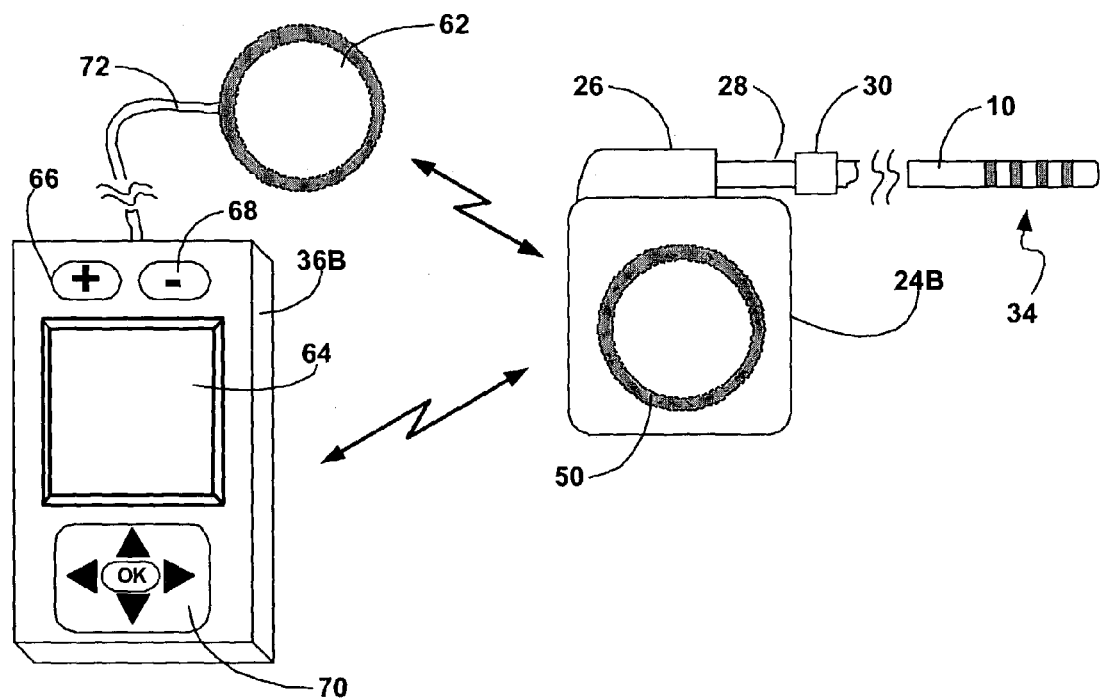
FIG. 8 is a diagram of an implantable trial neurostimulation device with a transcutaneous receiver coil interface for power delivery.

FIG. 8 is a diagram of an implantable trial neurostimulator 24B with a transcutaneous receiver coil 50 for power delivery. In particular, trial neurostimulator 36B includes a transcutaneous receiver coil 50, which either resides within or extends from a housing associated with the trial neurostimulator. Transcutaneous receiver coil 50 receives electromagnetic energy from transcutaneous transmitter coil 62, which may be integrated with patient programmer 36B or extend from a cable 72, as shown in FIG. 8. With the exception of transcutaneous transmitter coil 62, patient programmer 36B may otherwise conform to patient programmer 36A of FIG. 7.

Figure 9:
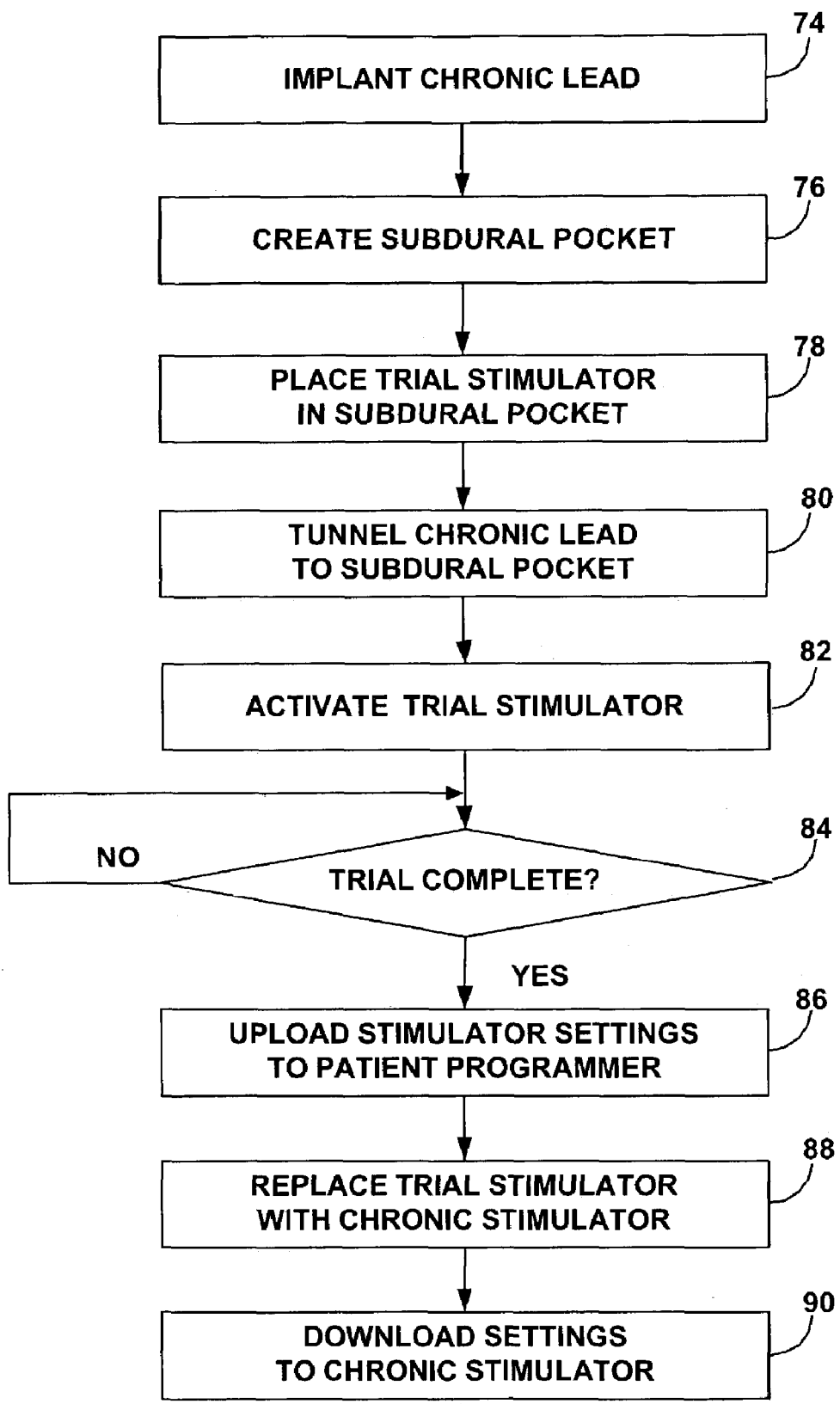
FIG. 9 is a flow diagram illustrating implantation and use of an implantable trial neurostimulator system.

FIG. 9 is a flow diagram illustrating implantation and use of an implantable trial neurostimulator system 21 in accordance with the invention. As shown in FIG. 9, a sacral stimulation lead 10 is first implanted (74), e.g., as shown in FIG. 1. Lead 10 may be chronic or temporary. With trial neurostimulator 24 implanted in the chronic implant site, however, it may be desirable to use the chronic lead and thereby avoid the need to withdraw a temporary lead and replace it with the chronic lead.

Upon creation of a subdural pocket (76), the trial neurostimulator is placed in the subdural pocket for implantation (78). The chronic lead is subcutaneously tunneled through the body of patient 12 to the subdural pocket (80). As shown in FIG. 2, for example, the lead may extend from sacrum 16 to a subdural pocket 31 in the upper left buttock area of patient 12.

When lead 10 is tunneled to subdural pocket 31, the lead is connected to trial neurostimulator 24 either directly or via a lead extension and connector. Before connecting lead 10 to trial neurostimulator 24, and tunneling the lead, a test stimulator may be connected to the lead to deliver neurostimulation for assistance in determining lead placement, lead depth and electrode selection.

Once the subdural pocket 31 is sealed, the trial neurostimulator 24 is activated for use in the trial period (82). Patient 12 thereafter goes about his daily routine, and may control trial neurostimulator 24 via patient programmer 36. When the trial is complete (84), e.g., as evidenced by expiration of a timer within trial neurostimulator 24 or patient programmer 36, or exhaustion of battery resources within the trial neurostimulator, the trial neurostimulator ceases operation.

Patient programmer 36, or physician programmer 34, then may upload from trial neurostimulator 24 a set of neurostimulator parameters, settings, operational information or the like either pre-programmed or accumulated during the course of the trial period (86). The information can be uploaded to patient programmer 36 either pre- or post-explant of trial neurostimulator 24.

If the results of the trial period are favorable, the physician replaces trial neurostimulator 24 with a chronic neurostimulator (88). In particular, the chronic neurostimulator may be placed in the same subdural pocket previously occupied by trial neurostimulator 24. In addition, the chronic neurostimulator can be connected to the proximal end of the chronic lead already residing within the subdural pocket.

Before or following implantation of the chronic neurostimulator, patient programmer 36 or physician programmer 34 downloads at least some of the parameters, settings, and other operational information uploaded from trial neurostimulator 24 (90). In this manner, patient programmer 36 or physician programmer 34 can be used to quickly and conveniently program the chronic neurostimulator based on the results of the trial period. This feature can greatly simplify programming of the chronic neurostimulator following the trial period.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for neurostimulation, as described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A method comprising:
   implanting a neurostimulation lead in a patient;
   implanting a trial neurostimulator in the patient;
   coupling the trial neurostimulator to the lead;
   removing the trial neurostimulator from the patient upon expiration of a trial period of times;
   implanting a chronic neurostimulator in the patient;
   removing the lead from the patient;
   implanting a second neurostimulation lead in the patient; and
   coupling the second neurostimulation lead to the chronic neurostimulator.

2. The method of claim 1, further comprising implanting the chronic neurostimulator in an implant site used for the implantation of the trial neurostimulator.

3. The method of claim 1, further comprising removing the trial neurostimulator when a battery within the trial neurostimulator is exhausted.

4. The method of claim 1, further comprising removing the trial neurostimulator within approximately one week following the implantation of the trial neurostimulator.

5. The method of claim 1, further comprising removing the trial neurostimulator within approximately one month following the implantation of the trial neurostimulator.

6. The method of claim 1, further comprising removing the trial neurostimulator within approximately six months following the implantation of the trial neurostimulator.

7. The method of claim 1, further comprising remotely disabling the trial neurostimulator upon expiration of the trial period of time.

8. The method of claim 1, further comprising uploading information from the trial neurostimulator, and downloading the information to the chronic neurostimulator.

9. The method of claim 8, wherein the information includes neurostimulation settings.

10. The method of claim 1, further comprising delivering power to the implanted trial neurostimulator transcutaneously, and terminating the delivery of power upon expiration of the trial period of time.

11. The method of claim 1, wherein the second lead is a sacral nerve stimulation lead.

12. The method of claim 1, wherein the trial neurostimulator is powered by a battery with a power rating of less than or equal to approximately 200 mAh.

* * * * *

UNITED STATES PATENT AND TRADEMARK OFFICE
CERTIFICATE OF CORRECTION

PATENT NO. : 7,065,412 B2  
APPLICATION NO. : 10/424032  
DATED : June 20, 2006  
INVENTOR(S) : Swoyer et al.

Page 1 of 1

It is certified that error appears in the above-identified patent and that said Letters Patent is hereby corrected as shown below:

Col. 10, Line 55: "period of times;" should read --period of time;--

Signed and Sealed this

Twenty-fifth Day of August, 2009

David J. Kappos  
*Director of the United States Patent and Trademark Office*